United States Patent [19]

Wingen et al.

[11] Patent Number: 4,465,758
[45] Date of Patent: Aug. 14, 1984

[54] 1,3-DIAZA-9-THIA-ANTHRACENE-2,4-DIONES AND PHOTOPOLYMERIZABLE MIXTURES CONTAINING SAME

[75] Inventors: Rainer Wingen, Frankfurt; Klaus Horn, Hofheim; Walter Lutz, Mainz-Kastel, all of Fed. Rep. of Germany

[73] Assignee: Hoechst Aktiengesellschaft, Frankfurt am Main, Fed. Rep. of Germany

[21] Appl. No.: 527,467

[22] Filed: Aug. 29, 1983

[30] Foreign Application Priority Data

Sep. 2, 1982 [DE] Fed. Rep. of Germany ....... 3232621

[51] Int. Cl.³ ..................... C07D 495/04; C08F 2/46; G03C 1/70
[52] U.S. Cl. .................................. 430/288; 544/249; 544/250; 204/159.16; 204/159.24; 430/915; 430/916; 430/920; 430/922; 430/910
[58] Field of Search ............... 544/249, 250, 279; 252/600; 204/159.16, 159.18, 159.24; 430/288, 915, 916, 920, 922, 910

[56] References Cited

U.S. PATENT DOCUMENTS 3,765,898 10/1973 Bauer et al. ..................... 96/115 P
4,189,366 2/1980 Newland ................... 204/159.24 X
4,296,196 10/1981 Faust .................................. 430/271

FOREIGN PATENT DOCUMENTS 1354541 5/1974 United Kingdom .

OTHER PUBLICATIONS

Fumio Yoneda, et al., "Synthesis and Properties of 1-Benzothiopyrano[2,3-d]-pyrimidine-2,4-(3H)diones (10-Thia-5-dezaflavins), Journal of Heterocyclic Chemistry, vol. 18, p. 1329, (1981).

*Primary Examiner*—John E. Kittle
*Assistant Examiner*—Cynthia Hamilton
*Attorney, Agent, or Firm*—Schwartz, Jeffery, Schwaab, Mack, Blumenthal & Koch

[57] ABSTRACT

Described are 1,3-diaza-9-thia-anthracene-2,4-diones of the general formula (II)

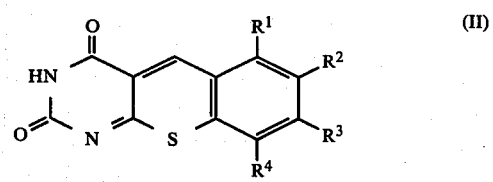

wherein
$R^1$, $R^3$ and $R^4$ are identical or different and individually each denotes a hydrogen or halogen atom, an alkyl, alkoxy, carboxyl or alkoxy-carbonyl group,
$R^2$ denotes an alkoxy, carboxyl or alkoxy-carbonyl group, or
two of the groups $R^1$, $R^2$, $R^3$, and $R^4$ together form a condensed aromatic radical.

These compounds are used as photoinitiators in photopolymerizable recording materials and have an increased sensitivity in the spectral range between 425 and 480 nm.

13 Claims, No Drawings

1,3-DIAZA-9-THIA-ANTHRACENE-2,4-DIONES AND PHOTOPOLYMERIZABLE MIXTURES CONTAINING SAME

BACKGROUND OF THE INVENTION

The present invention relates to novel 1,3-diaza-9-thia-anthracene-2,4-diones and to a photopolymerizable mixture which contains, as the essential components,
(a) a polymeric binder
(b) a polymerizable compound having at least two terminal, ethylenically unsaturated groups and a boiling point of more than 100° C., and
(c) a 1,3-diaza-9-thia-anthracene-2,4-dione as the photoinitiator.

Photopolymerizable mixtures which contain the components (a) and (b) and a polynuclear heterocyclic compound as the photoinitiator are known.

In German Pat. No. 20 27 467 (equivalent to British Patent Specification No. 1,354,541) specific derivatives of acridine and phenazine are described as initiators.

German Pat. No. 20 39 861 (equivalent to U.S. Pat. No. 3,765,898) discloses similar mixtures containing quinoxaline derivatives or quinazoline derivatives as initiators.

All these compounds act as excellent initiators when they are irradiated with actinic light, particularly from light sources emitting in the near ultraviolet range. But in recent times, metal halide-doped gas discharge lamps have become more and more commonly used for copying purposes because of their high luminous efficiency, and since these lamps have stronger emission values in the border range of the visible light, i.e., at about 400 nm and higher, than the hitherto conventionally used light sources, such as, for example, mercury vapor lamps, the absorption values of the known highly efficient initiators are no longer optimally matched to the emissions of these light sources. Moreover, the variations possible by substitution of the known heterocyclic initiators are limited, i.e., by means of known production processes it is possible to modify other properties, such as solubility in aqueous or organic solvents or compatibility with various photopolymerizable mixtures, to only a limited degree by a purposeful synthesis.

In the Journal of Heterocyclic Chemistry 18, p. 1,329 (1981), 1,3-diaza-9-thia-anthracene-2,4-diones are described which in their 6-position are either unsubstituted or substituted by a chlorine atom or a methyl group. In the publication, these components are tested for their oxidation capacity with respect of alcohols. Other uses are not mentioned.

SUMMARY OF THE INVENTION

Therefore, it is an object of the present invention to provide novel photoinitiators which possess a high efficiency like that of known photoinitiators, but which have light absorption values that extend more deeply into the short-wave visible range, and to which specific substituents can be purposefully attached in the course of their synthesis, which substituents impart various desired properties, to the final products, such as solubility and compatibility with other components.

It is also an object of the present invention to provide improved photopolymerizable compositions containing the novel photoinitiators of the invention.

In accomplishing these objects, there has been provided according to one aspect of the present invention a photopolymerizable mixture consisting essentially of:
(a) a polymeric binder
(b) a polymerizable compound having at least two terminal, ethylenically unsaturated groups and a boiling point of more than 100° C., and
(c) a polynuclear N-heterocyclic compound as photoinitiator.

The mixture of the invention is characterized in that the N-heterocyclic compound corresponds to the general formula (II)

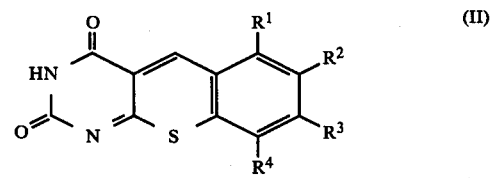

wherein $R^1$, $R^2$, $R^3$ and $R^4$ are identical or different and each denotes a hydrogen or halogen atom, an alkyl, alkoxy, carboxyl, or alkoxy-carbonyl group, or two of them together form a condensed aromatic radical.

In accordance with this invention, there are further provided novel 1,3-diaza-9-thia-anthracene-2,4-diones of the general formula (II)

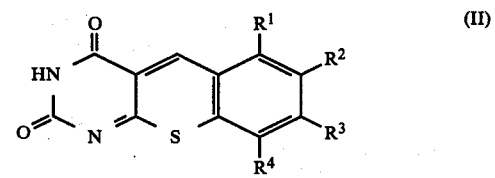

wherein
$R^1$, $R^3$ and $R^4$ are identical or different and each denotes a hydrogen or halogen atom, an alkyl, alkoxy, carboxyl, or alkoxy-carbonyl group,
$R^2$ denotes an alkoxy, carboxyl or alkoxy-carbonyl group, or
two of the groups $R^1$, $R^2$, $R^3$, and $R^4$ together form a condensed aromatic radical.

DETAILED DESCRIPTION OF PREFERRED EMBODIMENTS

The novel compounds can be prepared following the synthesis indicated by the following reaction summary:

2,4,6-trichloropyrimidine-5-carbaldehyde is reacted with an arylthiol in the presence of a tertiary amine. In this first step, HCL is split off from the reactants to form a 2,4-dichloro-6-arylthio-pyrimidine-5-carbaldehyde (I). In a second step, I is heated in concentrated sulfuric acid to form, with cyclization and generation of HCL, a 1,3-diaza-9-thia-anthracene-2,4-dione (II).

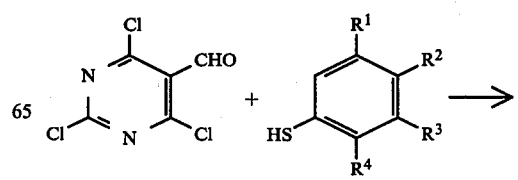

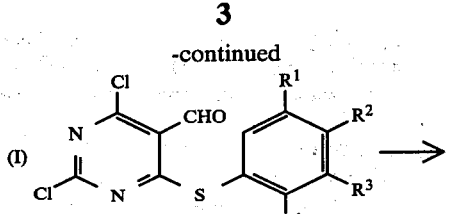

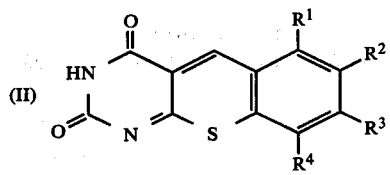

They absorb light in a spectral range of from about 425 to 480 nm and, when irradiated in this spectral range, act as active radical starters of the photopolymerization of vinyl compounds, even in the presence of oxygen. The novel photoinitiators do not initiate thermal polymerization of such compounds when there is no actinic radiation. Therefore, they are very well suited for the preparation of storable copying layers.

It is of advantage that compounds (II) can be produced by simple reactions using readily accessible educts known from literature, that the substituents $R^1$-$R^4$ can be varied within a wide range, and that purification is necessary only during the final stage.

Alkyl and alkoxy groups which can be used as possible substituents generally have 1 to 6, preferably 1 to 3, carbon atoms; methyl and methoxy groups are particularly preferred.

Fluorine, chlorine, and bromine atoms, in particular chlorine atoms, are the preferred halogen atoms. The alkoxy groups of the alkoxy-carbonyl groups may be the same as stated above. Benzo radicals are the particularly preferred condensed aromatic radicals.

Of the compounds according to the general formula (II), particularly preferred are those wherein at least one of the radicals $R^1$ to $R^4$ is a hydrogen atom. Compounds, wherein two or three of these radicals, particularly radicals $R^1$ to $R^3$, are hydrogen atoms, are especially preferred. If two of the radicals denote a benzo group, the two remaining radicals are preferably hydrogen atoms.

The added amount of photoinitiators in general varies between 0.01 and 10%, preferably between 0.1 and 5%, by weight, relative to the components of the photopolymerizable layer.

Photopolymerizable monomers useful for the purpose of this invention are known and are, for example, described in U.S. Pat. No. 2,760,863 and No. 3,060,023. Preferred examples are acrylic and methacrylic acid esters, such as diglycerol diacrylate, polyethylene glycol dimethacrylate, acrylates and methacrylates of trimethylol ethane, trimethylol propane, and pentaerythritol and polyhydric alicyclic alcohols. Reaction products of diisocyanates with partial esters of polyhydric alcohols are also used advantageously. Monomers of this kind are described in German Offenlegungsschriften No. 20 64 079, No. 23 61 041 and No. 28 22 190. The proportion of monomers contained in the layer in general varies between 10 and 80, preferably 20 and 60, percent by weight.

A great number of soluble organic polymers may be employed as binders. Examples are: polyamides, polyvinyl esters, polyvinyl acetals, polyvinyl ethers, epoxide resins, polyacrylic acid esters, polymethacrylic acid esters, polyesters, alkyd resins, polyacrylamide, polyvinyl alcohol, polyethylene oxide, polydimethyl acrylamide, polyvinyl pyrrolidone, polyvinylmethyl formamide, polyvinylmethyl acetamide, and copolymers of the monomers which form the enumerated homopolymers.

Other possible binders are natural substances or modified natural substances, for example, gelatin or cellulose ethers.

With particular advantage, those binders are used which are insoluble in water, but soluble or at least swellable in aqueous-alkaline solutions, since layers containing such binders can be developed with the preferably employed aqueous-alkaline developers. Binders of this type can, for example, contain the following groups: —COOH, —PO$_3$H$_2$, —SO$_3$H, —SO$_2$NH—, or —SO$_2$—NH—CO—. Examples of these are: maleate resins, polymers of β-methacryloyloxy-ethyl N-(p-tolyl-sulfonyl)-carbamate and copolymers of these and similar monomers with other monomers, and also styrene/maleic acid anhydride copolymers. Copolymers of alkylmethacrylates and methacrylic acid and copolymers of methacrylic acid, alkylmethacrylates and methyl methacrylates and/or styrene, acrylonitrile, and the like, which are described in German Offenlegungsschrift No. 20 64 080 and German Offenlegungsschrift No. 23 63 806, are preferably used.

In general, the added quantity of binder amounts to 20 to 90%, preferably 40 to 80%, by weight of the layer constituents.

Depending on their intended use and desired properties, the photopolymerizable mixtures may contain various additional substances. Examples of these admixtures are:
  inhibitors to prevent thermal polymerization of the monomers,
  hydrogen donors,
  substances regulating the sensitomeric
  properties of layers of this type,
  dyes,
  colored and uncolored pigments,
  color formers,
  indicators,
  plasticizers, etc.

These constituents advantageously should be selected to minimize absorption in the range of actinic radiation, which is important for the initiation process.

Within the scope of this invention, actinic radiation is to be understood as any radiation, the energy of which corresponds at least to that of short-wave visible light. Longwave UV-radiation, as well as electron radiation, X-rays, and laser radiation, is suitable.

The photopolymerizable mixtures of this invention can be used in many fields of application, such as the production, for example, of safety glass, varnishes which are hardened by the action of light or corpuscular radiation, such as electron beams, and dental fillings and, in particular, as a light-sensitive copying material in the field of reproduction.

The detailed description of preferred embodiments of the invention is directed to this last field of application, but without the invention being limited thereto. Examples of possible applications in this field are: copying layers for the photomechanical production of printing forms suitable for relief printing, lithographic printing, gravure printing, or screen printing; relief copies, for example, in the production of Braille books; single copies; tanned images; pigment images; etc. The mixtures may further be employed for the photomechanical production of etch resists, for example, for name plates, printed circuits, and chemical milling. The mixtures of this invention are of particular importance with regard to the photomechanical production of lithographic printing forms and etch resists, especially in the form of presensitized materials.

The mixture can be used industrially for the above mentioned applications as a liquid solution or dispersion, for example, a photoresist solution, which is applied by the consumer to an appropriate support, for example, for chemical milling, for the production of printed circuits, screen printing stencils, etc. The mixtures may also be present as a solid light-sensitive layer on a suitable support, i.e., as a storable, presensitized copying material, for example, for the production of printing forms. It can also be employed for the production of dry resists.

It is in general advantageous to substantially isolate the mixtures from the influence of atmospheric oxygen during the light polymerization. If the mixture is used in the form of thin copying layers, it is recommended to apply a suitable cover film which has a low permeability to oxygen. The cover film may be self-supporting and be removed from the copying layer prior to development. Polyester films, for example, are suitable for this purpose. The cover film may also consist of a material which dissolves in the developer liquid or which can be removed at least from the non-hardened areas during development. Examples of materials suitable for this purpose are, inter alia, waxes, polyvinyl alcohol, polyphosphates, sugars, etc.

Layer supports which are suitable for copying materials prepared using the mixture of this invention include, for example, aluminum, steel, zinc, copper, plastic films, such as films of polyethylene terephthalate or cellulose acetate, and screen printing supports, such as perlon gauze.

The light-sensitive materials employing the mixture of this invention are conventionally prepared. Thus, the mixture can be taken up in a solvent, and the resulting solution or dispersion can be applied to the intended support as a thin film by casting, spraying, immersion, or roller application and subsequently dried. Thick layers (for example, of 250 µm and thicker) are advantageously prepared by first producing a self-supporting film by extrusion or molding, which is then laminated to the support. In the case of dry resists, solutions of the mixture are applied to transparent intermediate supports and dried. The light-sensitive layers, having a thickness between about 10 and 100 µm, are then also bonded to the desired support, by lamination together with the temporary support.

The copying materials can be processed using known methods. They are developed by treatment with an appropriate developer solution, preferably a weakly alkaline solution, whereby the unexposed areas of the layer are dissolved away and the exposed areas of the copying layer remain on the support.

The following text presents examples of the mixture of the present invention. First, the production of a number of novel photoinitiators according to the invention is described.

In the production formulations and the Examples which follow, parts by weight (p.b.w.) and parts by volume (p.b.v.) bear the same relationship as the g and the $cm^3$ are related to each other. Unless otherwise stated, percentages and quantities are to be understood as weight units.

Most of the initiators contained in the mixture of this invention are not known from prior publications. They are produced in accordance with the following procedure:

(A)

General procedure for producing compounds of formula I (see Figure)

1 mole of 2,4-6-trichloropyrimidine-5-carbaldehyde is reacted with 1 mole of arylthiol and 1.1 moles of triethyl amine, in tetrahydrofuran, at temperatures of $-50°$ to $-30°$ C.; then the amine hydrochloride is separated off by filtration, and the residue left after removing the solvent from the filtrate by distillation is crystallized by mixing with an appropriate solvent. The 2,4-dichloro-6-arylthiopyrimidine-5-carbaldehydes (compounds 1 to 31) thus obtained tend to decompose in the solid state and, therefore, are immediately processed. Accordingly, the figures in Table 1 denote the raw yields.

TABLE I

| No. | $R^1$ | $R^2$ | $R^3$ | $R^4$ | Yield % |
|---|---|---|---|---|---|
| 1 | H | H | H | H | 71.9 |
| 2 | H | H | H | $CH_3$ | 34.8 |
| 3 | H | H | $CH_3$ | H | 52.5 |
| 4 | H | $CH_3$ | H | H | 63.8 |
| 5 | H | F | H | H | 56.1 |
| 6 | H | H | H | Cl | 54.1 |
| 7 | H | H | Cl | H | 56.1 |
| 8 | H | Cl | H | H | 40.7 |
| 9 | H | Br | H | H | 69.1 |
| 10 | H | H | H | $OCH_3$ | 66.0 |
| 11 | H | H | H | COOH | 75.9 |
| 12 | H | H | H | $COOCH_3$ | 61.0 |
| 13 | H | COOH | H | H | 31.3 |
| 14 | H | H | $CH_3$ | $CH_3$ | 25.5 |
| 15 | H | $CH_3$ | H | $CH_3$ | 57.5 |
| 16 | $CH_3$ | H | H | $CH_3$ | 56.8 |
| 17 | H | H | Cl | $CH_3$ | 72.2 |
| 18 | H | Cl | H | $CH_3$ | 65.9 |
| 19 | Cl | H | H | $CH_3$ | 67.7 |
| 20 | H | H | $CH_3$ | Cl | 82.1 |
| 21 | H | $CH_3$ | H | Cl | 66.9 |
| 22 | H | H | Cl | Cl | 39.1 |
| 23 | Cl | H | H | Cl | 67.6 |
| 24 | Cl | H | Cl | H | 71.7 |
| 25 | $CH_3$ | $CH_3$ | H | $CH_3$ | 45.2 |
| 26 | $CH_3$ | Cl | H | $CH_3$ | 57.5 |
| 27 | $CH_3$ | Cl | H | Cl | 56.8 |
| 28 | H | Cl | Cl | Cl | 53.7 |
| 29 | Cl | Cl | H | Cl | 33.5 |
| 30 | H | H | benzo | | 40.1 |
| 31 | benzo | | H | H | 76.1 |

General procedure used for producing the compounds of formula II 1 p.b.w. of one of the compounds 1 to 31 is strewed in 20 p.b.w. of $H_2SO_4$ (98%) at a temperature of 70° C., the mixture is heated to 110° to 150° C. until the formation of HCl is completed; then the mixture is poured onto 120 p.b.w. of ice, adjusted to a pH of 4 at temperatures of 30° C. to 40° C. by means of an alkali compound, and the solids are separated off, dried and recrystallized from dimethyl formamide.

TABLE 2

1,3-diaza-9-thia-anthracene-2,4-diones of the formula II

| No. | $R^1$ | $R^2$ | $R^3$ | $R^4$ | Melting Point °C. | Yield % |
|---|---|---|---|---|---|---|
| 32 | H | H | H | H | 290 | 62.3 |
| 33 | H | H | CH$_3$ | H | 300 | 68.4 |
| 34 | H | H | H | CH$_3$ | 300 | 64.8 |
| 35 | H | F | H | H | 280 | 11.5 |
| 36 | H | Cl | H | H | 300 | 17.6 |
| 37 | H | H | H | Cl | 290 | 50.7 |
| 38 | H | Br | H | H | 280 | 10.5 |
| 39 | H | H | H | COOH | 280 | 21.6 |
| 40 | H | H | H | COOCH$_3$ | 270 | 5.2 |
| 41 | CH$_3$ | H | H | CH$_3$ | 270 | 22.2 |
| 42 | H | CH$_3$ | H | CH$_3$ | 310 | 6.6 |
| 43 | H | H | CH$_3$ | CH$_3$ | 270 | 6.8 |
| 44 | Cl | H | H | CH$_3$ | 290 | 52.7 |
| 45 | H | Cl | H | CH$_3$ | 300 | 35.9 |
| 46 | H | CH$_3$ | H | Cl | 290 | 47.8 |
| 47 | Cl | H | Cl | H | 210 | 42.3 |
| 48 | Cl | H | H | Cl | 270 | 49.7 |
| 49 | CH$_3$ | CH$_3$ | H | CH$_3$ | 300 | 9.7 |
| 50 | CH$_3$ | Cl | H | CH$_3$ | 350 | 54.0 |
| 51 | CH$_3$ | Cl | H | Cl | 280 | 11.2 |
| 52 | Cl | Cl | H | Cl | 280 | 3.2 |
| 53 | benzo | | H | H | 300 | 42.8 |
| 54 | H | H | benzo | | 290 | 42.8 |

The initiating activity of the compounds nos. 32 to 54 is tabularly compiled in a series of Examples which follow.

EXAMPLE 1

A solution of
- 4.0 p.b.w. of a methylmethacrylate/methacrylic acid copolymer (acid number about 110)
- 4.0 p.b.w. of trimethylolethanetriacrylate,
- 0.08 p.b.w. of a blue azo dyestuff obtained by coupling 2,4-dinitro-6-chlorobenzene diazonium salt with 2-methoxy-5-acetylamino-N-cyanoethyl-N-hydroxyethylaniline, and
- 0.21 p.b.w. of initiator, in
- 38 p.b.w. of ethyleneglycol monoethyl ether and
- 18 p.b.w. of butyl acetate is spin-coated onto electrolytically roughened and anodically oxidized, 0.3 mm thick aluminum and dried, in a way such that a dry layer weight of 25 g/m$^2$ is obtained.

After drying, the photopolymer layer is provided with a coating comprised of a solution of
- 5 p.b.w. of polyvinyl alcohol (12% residual acetyl groups, K-value 8), in
- 95 p.b.w. of purified water and dried, so that a peelable cover layer having a weight of about 5 g/m$^2$ is obtained.

Subsequently, the plate is exposed for 40 seconds by means of a 5 kW metal halide lamp, through a 13-step exposure wedge. After exposure, the plate is heated to 120° C. for 1 minute. Then the exposed photopolymer layer is developed for about 1 minute with a developer of:
- 1.5 p.b.w. of sodium metasilicate×9H$_2$O
- 0.01 p.b.w. of a polyoxyethylene ether of coconut fatty alcohol having about 8 oxyethylene units, and
- 98.3 p.b.w. of purified water, using a cotton pad.

The plate is rinsed with water and rendered acidic with 1% strength phosphoric acid and inked with a greasy ink.

After inking, the plate is treated with a commercially available desensitizing gumming solution and dried. On an offset press about 100,000 prints can be run.

The following light sensitivities are measured:

| Compound | Developed solid steps |
|---|---|
| 32 | 2 |
| 33 | 3 |
| 34 | 2 |
| 35 | 1 |
| 36 | 1 |
| 37 | 5 |
| 38 | 2 |
| 39 | 3 |
| 40 | 2 |
| 41 | 2 |
| 42 | 1 |
| 43 | 2–3 |
| 44 | 4 |
| 45 | 4 |
| 46 | 4 |
| 47 | 2–3 |
| 48 | 5 |
| 49 | 2 |
| 50 | 2 |
| 51 | 1 |
| 52 | 2 |
| 53 | 1 |
| 54 | 2–3 |

EXAMPLE 2

7 solutions, which are each composed of
- 5.6 p.b.w. of the product obtained by reacting 1 mole of 2,2,4-trimethyl-hexamethylene diisocyanate with 2 moles of 2-hydroxy-ethyl methacrylate,
- 6.5 p.b.w. of a terpolymer of styrene, n-hexylmethacrylate and methacrylic acid (10:60:30),
- 0.2 p.b.w. of one of the compounds 33, 37, 39, 44, 45, 46, and 48
- 0.15 p.b.w. of triethylene glycol dimethacrylate, and
- 0.035 p.b.w. of the blue azo dyestuff described in Example 1, in
- 30 p.b.w. of butanone and
- 0.5 p.b.w. of ethyl alcohol are successively spin-coated onto 25 μm thick polyethylene terephthalate film, in a way such that a 25 μm thick layer (30 g/m$^2$) is obtained. Then the plates are dried in a drying cabinet at 100° C. for 2 minutes.

For protection from damage or dust contamination, the layers thus produced are covered with a cover film having a thickness of 20–25 μm, whereby the adhesion between the cover film and the light-sensitive layer is smaller than the adhesion between the layer and the polyester support. Thus treated, the plates can be stored over a relatively long period of time.

The copper surface of a phenoplast laminate plate, to which a 35 μm thick copper foil is bonded, is mechanically cleaned with pumice powder or a brushing machine and blown dry with oil-free air after thorough rinsing with water.

The cover film is peeled off, and the dry resist is laminated onto the cleaned copper plates by means of a laminating device equipped with heated rolls, at a temperature of 120° C. and a speed of 1.5 m/min.

Then the seven samples are exposed through the support film, under a 13-step exposure wedge having density increments of 0.15. Exposure is performed by means of a 5 kW metal halide lamp, the exposure times are 10, 20 and 40 seconds.

The wedge step 0 corresponds to an optical density of 0.05 (auto-absorption of the film material).

After removal of the support film, the plates are spray-developed with an 0.8% sodium carbonate solution. The developing time is about 60 seconds at a temperature of 23° C.

In order to test the developer resistance—it is the purpose of this test to find out whether the wedge steps are completely cross-linked—the samples are subjected to the threefold developing time, i.e., 180 seconds, after exposure for 20 seconds.

In the following table, the completely cross-linked wedge steps of the dry resist layers are compiled, the layers differing from one another merely by the photo-initiator used in each case:

| Compound | Solid steps in the sprayer at | | | Solid steps at 180 sec. development |
| | 10 sec | 20 sec exposure | 40 sec | |
|---|---|---|---|---|
| 33 | — | 1 | 3 | — |
| 37 | 2 | 4 | 6 | 3 |
| 39 | — | 1 | 3 | — |
| 44 | 1 | 3 | 5 | 2 |
| 45 | 1 | 3 | 5 | 2 |
| 46 | 1 | 3 | 5 | 2 |
| 48 | 2 | 4 | 6 | 3 |

EXAMPLE 3

0.4 g each of the compounds 37 and 48 are added to photopolymer mixtures, as described in Example 2, and the solutions are spin-coated onto 25 μm thick polyethylene terephthalate films, in a way such that 25 μm thick layers (30 g/m²) are obtained.

Following the procedure of Example 2, the layers are then applied to the cleaned copper surfaces of 10 cm×15 cm Cu-phenolic resin laminate plates, exposed through the support film and developed with an 8% aqueous sodium carbonate solution.

The following numbers of completely cross-linked wedge steps result (comparison: number of solid steps when each solution contains 0.6 g of initiator):

| compound | Solid steps with 0.4 g of initiator Exposure time (sec) | | | Comparison: Solid steps with 0.6 g of initiator Exposure time (sec) | | |
| | 10 | 20 | 40 | 10 | 20 | 40 |
|---|---|---|---|---|---|---|
| 37 | 3 | 6 | 8 | 2 | 3 | 5 |
| 48 | 3 | 5 | 7 | 2 | 4 | 6 |

EXAMPLE 4

A solution of
1.0 p.b.w. trimethylolethane triacrylate,
1.4 p.b.w. of a terpolymer comprised of n-hexyl methacrylate, methyl methacrylate and methacrylic acid (50:25:25) and having an acid numer of about 160,
0.02 p.b.w. of Sudan Blue II, and
0.05 p.b.w. of compound 37, in
6.0 p.b.w. of butanone is spin-coated onto a cleaned single-stage zinc etch plate and dried, in a way such that a layer weight of about 10 g/m² is obtained.

Thereafter, the copying material is provided with a 1-2 μm thick coating of polyvinyl alcohol, dried and exposed for 40 seconds under a positive original using a 5 kW metal halide lamp. The zinc plate is developed for 45 seconds with a developer composed of
1.5 p.b.w. of sodium metasilicate nonahydrate
0.3 p.b.w. of polyglycol 6,000
0.3 p.b.w. of levulinic acid
0.3 p.b.w. of strontium hydroxide×8H₂O, and
97.6 p.b.w. of purified water.

After thorough rinsing with water, etching is performed for 5 minutes with 10% strength nitric acid containing an edge protecting agent. The hardened photopolymer layer is removed with ethyleneglycol monobutyl ether. The printing form obtained can be used for high quality book printing.

EXAMPLE 5

A coating solution as described in Example 4, but containing 0.05 p.b.w. of compound 48 instead of compound 37, is applied by casting to a 25 μm thick polyethylene terephthalate film, in a way such that a 20 μm thick layer (26 g/m²) is obtained. Then drying is performed at 100° C. in a drying cabinet for 2 minutes.

Together with the polyester film, the dried layer is laminated onto a screen printing cloth VS Monoprint P 77 made by Verseidag, Krefeld, by means of a laminating device employing the highest possible pressure, a temperature of 115° C., and a speed of 1 m/min.

Thereafter, exposure is performed under a positive original for 60 seconds through the polyester film, by means of a 5 kW metal halide lamp.

The polyester film is removed and the non-cross-linked image areas are removed with the developer described in Example 4 in a swing bath within 45 seconds. After thorough rinsing with water and drying, the screen printing form is ready for use.

What is claimed is:

1. A photopolymerizable mixture consisting essentially of:
   (a) a polymeric binder,
   (b) a polymerizable compound having at least two terminal ethylenically unsaturated groups and a boiling point of more than 100° C., and
   (c) a polynuclear N-hetercyclic compound of the general formula (II) as a photoinitiator

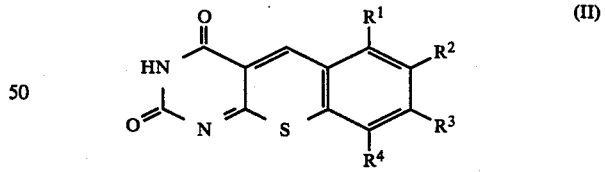

wherein $R^1$, $R^2$, $R^3$ and $R^4$ are identical or different and each denotes a hydrogen or halogen atom, an alkyl, alkoxy, carboxyl, or alkoxy-carbonyl group, or two of them together form a condensed aromatic radical.

2. A photopolymerizable mixture as in claim 1, wherein at least one of the radicals $R^1$ to $R^4$ is a hydrogen atom.

3. A photopolymerizable mixture as in claim 2, wherein two or three of the radicals $R^1$ to $R^3$ are hydrogen atoms.

4. A photopolymerizable mixture as in claim 3, wherein two of $R^1$ to $R^4$ are benzo groups and the remaining radicals are hydrogen.

5. A photopolymerizable mixture as in claim 1, wherein said alkyl and alkoxy groups of $R^1$ to $R^4$ have 1 to 3 carbon atoms.

6. A photopolymerizable mixture as in claim 1, wherein said halogen atom of $R^1$ to $R^4$ is fluorine, chlorine, or bromine.

7. A photopolymerizable mixture as in claim 1, wherein said condensed aromatic radical is a benzo radical.

8. A photopolymerizable mixture as in claim 1, wherein said polymeric binder is soluble or swellable in aqueous solutions.

9. A photopolymerizable mixture as in claim 8, wherein said polymeric binder is a copolymer selected from the group consisting of copolymers of alkylmethacrylates, methyl methacrylate, methacrylic acid and/or styrene.

10. A compound of the general formula

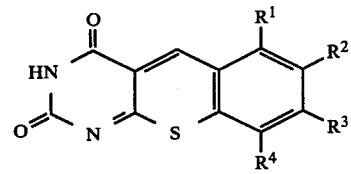

(II)

wherein
$R^1$, $R^3$ and $R^4$ are identical or different and each denotes a hydrogen or halogen atom, an alkyl, alkoxy, carboxyl or alkoxy-carbonyl group,
$R^2$ denotes an alkoxy, carboxyl or alkoxy-carbonyl group, or
two of the groups $R^1$, $R^2$, $R^3$, and $R^4$ together form a condensed aromatic radical.

11. A compound as in claim 10, wherein said alkyl and alkoxy groups of $R^1$, $R^3$, and $R^4$ and said alkoxy group of $R^2$ have 1 to 3 carbon atoms.

12. A compound as in claim 10, wherein said halogen atom of $R^1$, $R^3$, and $R^4$ is fluorine, chlorine, or bromine.

13. A compound as in claim 10, wherein said condensed aromatic is a benzo radical.

* * * * *